United States Patent
Honma (12)

(10) Patent No.: US 10,092,166 B2
(45) Date of Patent: Oct. 9, 2018

(54) IMAGE PROCESSING DEVICE AND IMAGE PROCESSING METHOD FOR COLOR CALIBRATION OF AN IMAGE

(71) Applicant: Sony Corporation, Tokyo (JP)

(72) Inventor: Hiroe Honma, Kanagawa (JP)

(73) Assignee: Sony Corporation, Tokyo (JP)

( * ) Notice: Subject to any disclaimer, the term of this patent is extended or adjusted under 35 U.S.C. 154(b) by 245 days.

(21) Appl. No.: 14/222,141

(22) Filed: Mar. 21, 2014

(65) Prior Publication Data

US 2014/0293031 A1 Oct. 2, 2014

(30) Foreign Application Priority Data

Mar. 28, 2013 (JP) ................................ 2013-068826

(51) Int. Cl.
| | |
|---|---|
| H04N 7/18 | (2006.01) |
| A62B 1/04 | (2006.01) |
| H04N 3/28 | (2006.01) |
| A61B 1/00 | (2006.01) |
| H04N 5/225 | (2006.01) |
| H04N 9/04 | (2006.01) |
| H04N 9/73 | (2006.01) |

(52) U.S. Cl.
CPC ...... A61B 1/00057 (2013.01); A61B 1/00045 (2013.01)

(58) Field of Classification Search
CPC ............ H04N 7/18; H04N 3/28; H04N 5/225; H04N 9/04; H04N 9/73; A62B 1/04
USPC .......... 348/61, 65, 71, 206, 207.99, 207.32, 348/223.1, 225.1, 45
See application file for complete search history.

(56) References Cited

U.S. PATENT DOCUMENTS

| | | | | |
|---|---|---|---|---|
| 5,889,929 | A * | 3/1999 | Hori ..................... | H04N 1/6052 358/1.1 |
| 6,184,939 | B1 * | 2/2001 | Wang ...................... | H04N 5/14 348/537 |
| 2003/0160900 | A1 * | 8/2003 | Dumitras ................. | H04N 9/68 348/649 |
| 2005/0099431 | A1 * | 5/2005 | Herbert .................... | G06F 3/14 345/601 |
| 2010/0328535 | A1 * | 12/2010 | Okui ....................... | G09G 3/20 348/578 |

FOREIGN PATENT DOCUMENTS

JP 2008-099881 A 5/2006

* cited by examiner

*Primary Examiner* — Daquan Zhao
(74) *Attorney, Agent, or Firm* — Chip Law Group

(57) ABSTRACT

There is provided an image processing device including an image information acquisition unit configured to acquire a captured image from an endoscope, an adjustment information acquisition unit configured to acquire color calibration information about color calibration performed in a display device on which the captured image is displayed, a transmission unit configured to transmit, to a printing device, print data corresponding to the acquired captured image, and a correction value acquisition unit configured to acquire a correction value used for performing, on the print data, correction that is corresponding to the color calibration of the acquired color calibration information.

15 Claims, 10 Drawing Sheets

FIG. 4
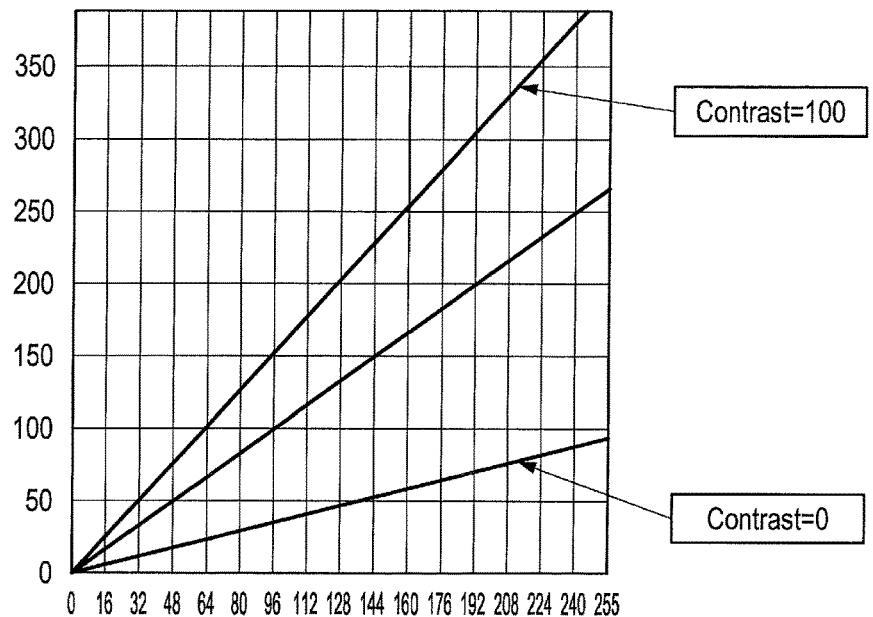
(a)
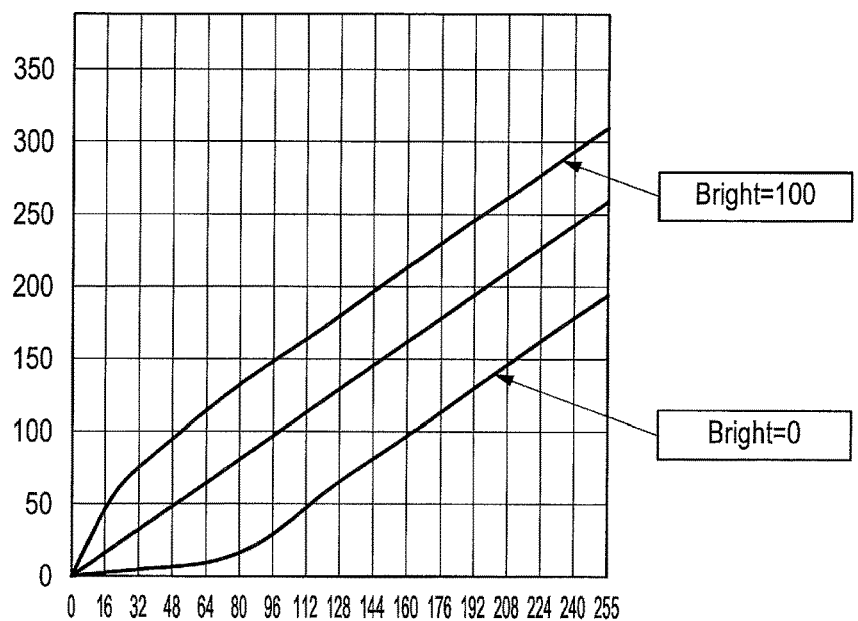
(b)

FIG. 5
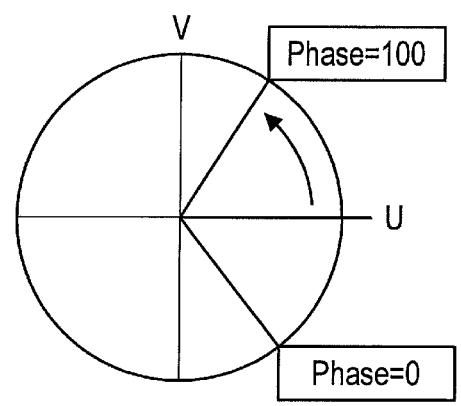
(a)
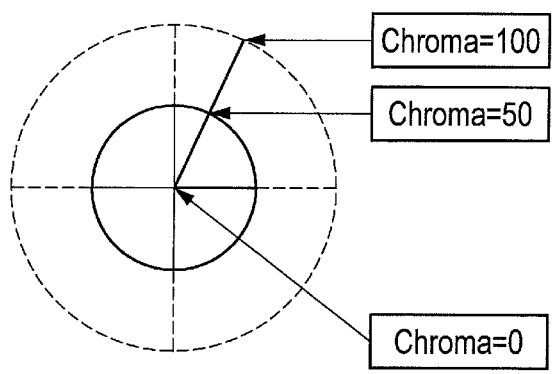
(b)

IMAGE PROCESSING DEVICE AND IMAGE PROCESSING METHOD FOR COLOR CALIBRATION OF AN IMAGE

CROSS REFERENCE TO RELATED APPLICATIONS

This application claims the benefit of Japanese Priority Patent Application JP 2013-068826 filed Mar. 28, 2013, the entire contents of which are incorporated herein by reference.

BACKGROUND

The present disclosure relates to an image processing device, an image processing method, a program, and an endoscope system.

In recent years, an endoscope system including an endoscope, a display device, a printing device, and a controller has been proposed as a diagnostic imaging device. In the endoscope system, the display device can display an image captured by the endoscope, and a printing device can perform printing (see JP 2008-99881A).

SUMMARY

Before shipment, the display device and the printing device in the above-described endoscope system are subjected to color calibration. However, after shipment, a user may further adjust an image quality in the display device to obtain a desirable image quality, depending on the situation.

However, even if the color calibration is performed in the display device, the color calibration is not reflected in the whole system, and the color calibration is performed only in the display device. Accordingly, a gap between an image quality of an image printed by the printing device and an image quality in the display device occurs. In this case, the user has to perform color calibration in the printing device by trial and error so as to make the color calibration in the printing device correspond with the color calibration in the display device in order to overcome the gap between the images.

Accordingly, the present disclosure proposes a method for suppressing occurrence of a gap between an image quality in a display device and an image quality in a printing device even if a user performs color calibration in the display device.

According to an embodiment of the present disclosure, there is provided an image processing device including an image information acquisition unit configured to acquire a captured image from an endoscope, an adjustment information acquisition unit configured to acquire color calibration information about color calibration performed in a display device on which the captured image is displayed, a transmission unit configured to transmit, to a printing device, print data corresponding to the acquired captured image, and a correction value acquisition unit configured to acquire a correction value used for performing, on the print data, correction that is corresponding to the color calibration of the acquired color calibration information.

According to an embodiment of the present disclosure, there is provided an image processing method including acquiring a captured image from an endoscope, acquiring color calibration information about color calibration performed in a display device on which the captured image is displayed, transmitting, to a printing device, print data corresponding to the acquired captured image, and acquiring a correction value used for performing, on the print data, correction that is corresponding to the color calibration of the acquired color calibration information.

According to an embodiment of the present disclosure, there is provided a program for causing a computer to execute, acquiring a captured image from an endoscope, acquiring color calibration information about color calibration performed in a display device on which the captured image is displayed, transmitting, to a printing device, print data corresponding to the acquired captured image, and acquiring a correction value used for performing, on the print data, correction that is corresponding to the color calibration of the acquired color calibration information.

According to an embodiment of the present disclosure, there is provided an endoscope system including a display device configured to display a captured image captured by an endoscope, a printing device configured to perform printing, and an image processing device configured to transmit, to the printing device, print data corresponding to the captured image. The image processing device includes an image information acquisition unit configured to acquire the captured image from the endoscope, an adjustment information acquisition unit configured to acquire color calibration information about color calibration performed in a display device on which the captured image is displayed, and a correction value acquisition unit configured to acquire a correction value used for performing, on the print data, correction that is corresponding to the color calibration of the acquired color calibration information.

According to one or more of embodiments of the present disclosure, it is possible to suppress occurrence of a gap between an image quality in a display device and an image quality in a printing device even if a user performs color calibration in the display device.

BRIEF DESCRIPTION OF THE DRAWINGS

FIG. 4 is a schematic view illustrating the contrast processing and the bright processing.

FIG. 5 is a schematic view illustrating phase processing and chroma processing;

DETAILED DESCRIPTION OF THE EMBODIMENT(S)

Figure 1:
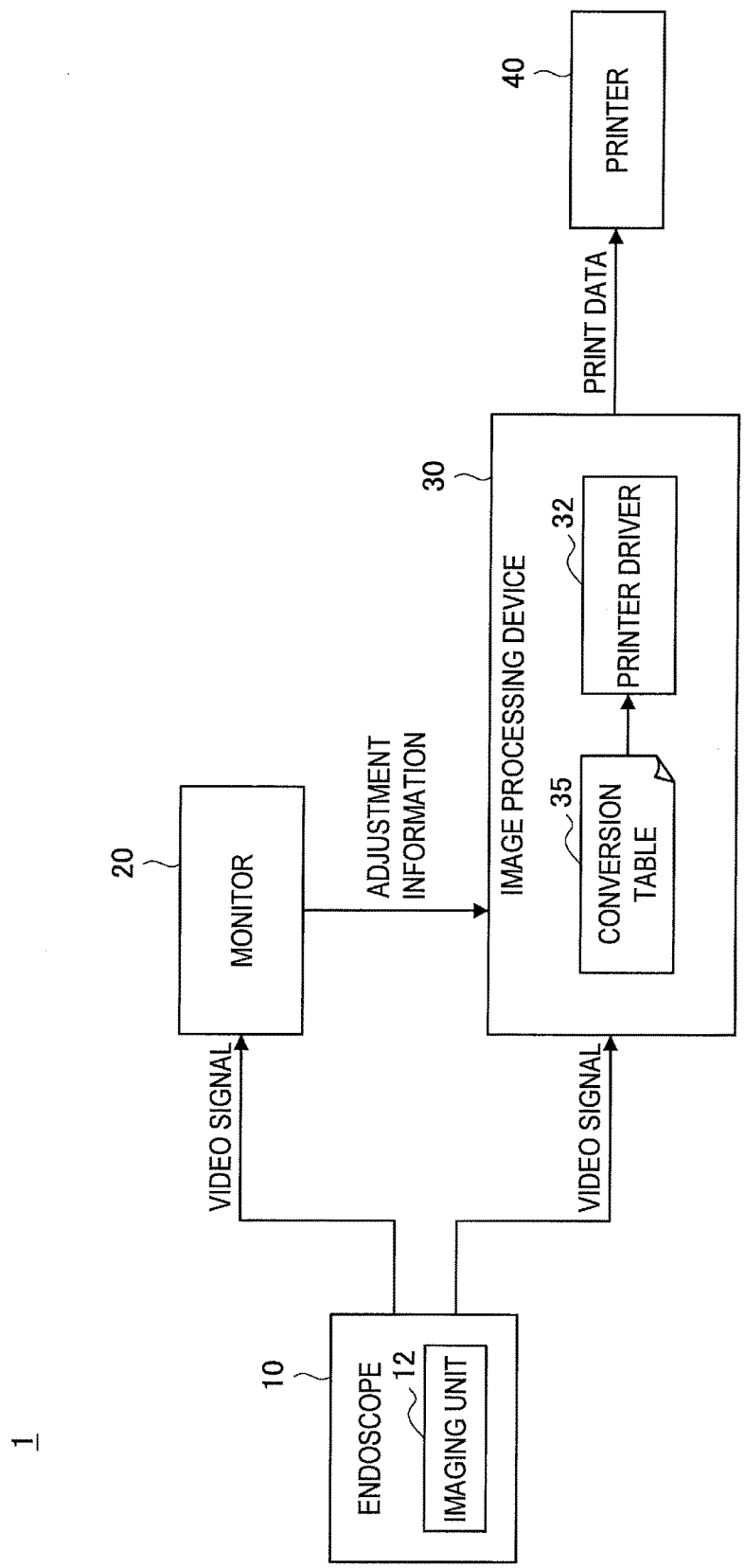
FIG. 1 is a block diagram showing an example of a schematic configuration of an endoscope system 1 according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. First Embodiment
1-1. Endoscope System
1-2. Functional Configuration of Image Processing Device
1-3. Operation Example of Image Processing Device
2. Second Embodiment
3. Third Embodiment
4. Hardware Configuration
5. Conclusion 1. First Embodiment (1-1. Endoscope System)

With reference to FIG. 1, there will be described a configuration of an endoscope system according to a first embodiment of the present disclosure.

FIG. 1 is a block diagram showing an example of a schematic configuration of an endoscope system 1 according to a first embodiment of the present disclosure. As shown in FIG. 1, the endoscope system 1 includes an endoscope 10, a monitor 20, an image processing device 30, and a printer 40.

The endoscope 10 includes an imaging unit 12 in which image sensors are loaded, and the endoscope 10 photographs, when inserted into a body of a patient or the like, an inside of the human body. The endoscope 10 is communicably connected with the monitor 20, the image processing device 30 and the like via wire or radio. The endoscope 10 outputs a captured image to the monitor 20 and the image processing device 30. For example, the endoscope 10 is an electronic scope which can be operated by a surgeon (user). Note that, the configuration is not limited thereto. For example, the endoscope 10 may be a capsule-type endoscope.

The monitor 20 is a display device to display various types of information and images. The monitor 20 receives a captured image (video signal) captured by the endoscope 10, and displays the captured image. For example, the monitor 20 is a liquid crystal display. The monitor 20 is communicably connected with the image processing device 30. For example, the monitor 20 transmits device information (model information) of the monitor 20 to the image processing device 30.

The image processing device 30 performs predetermined image processing on the captured image (video signal) received from the endoscope 10. The image processing device 30 is communicably connected with the printer 40. The image processing device 30 performs image processing on the captured image. In addition, the image processing device 30 includes a printer driver 32 and generates print data that the printer 40 can print by using a conversion table 35 (so-called LUT) for a printer. Subsequently, the image processing device 30 transmits the print data (print data corresponding to the captured image) subjected to image processing to the printer 40. A detailed configuration of the image processing device 30 will be described below.

The printer 40 prints the print data received from the image processing device 30. For example, the printer 40 prints the captured image displayed on the monitor 20. For example, the printer 40 is a laser printer or an inkjet printer.

In embodiments of the present disclosure, a user can adjust an image quality (for example, colors in an image) on the monitor 20. For example, the user adjusts contrast and brightness of the image in order to improve the visualization. When the user performs the adjustment of the image quality, the monitor 20 transmits adjustment information to the image processing device 30.

When receiving the adjustment information about the adjustment of the image quality of the monitor 20, the image processing device 30 performs, on the print data transmitted to the printer 40, correction that is corresponding to the adjustment of the image quality on the basis of the adjustment information. Accordingly, the image quality of the image being displayed on the monitor 20 becomes the same as an image quality of an image printed by the printer 40. In this way, even if the user does not adjust the image quality of the printer 40, the adjustment of the printer 40 is automatically performed on the basis of the adjustment of the image quality of the monitor 20. Accordingly, convenience is improved.

Although, in the above description, the monitor 20 directly receives the captured image from the endoscope 10, the configuration is not limited thereto. For example, the monitor 20 may receive the captured image through the image processing device 30.

(1-2. Functional Configuration of Image Processing Device)

Figure 2:
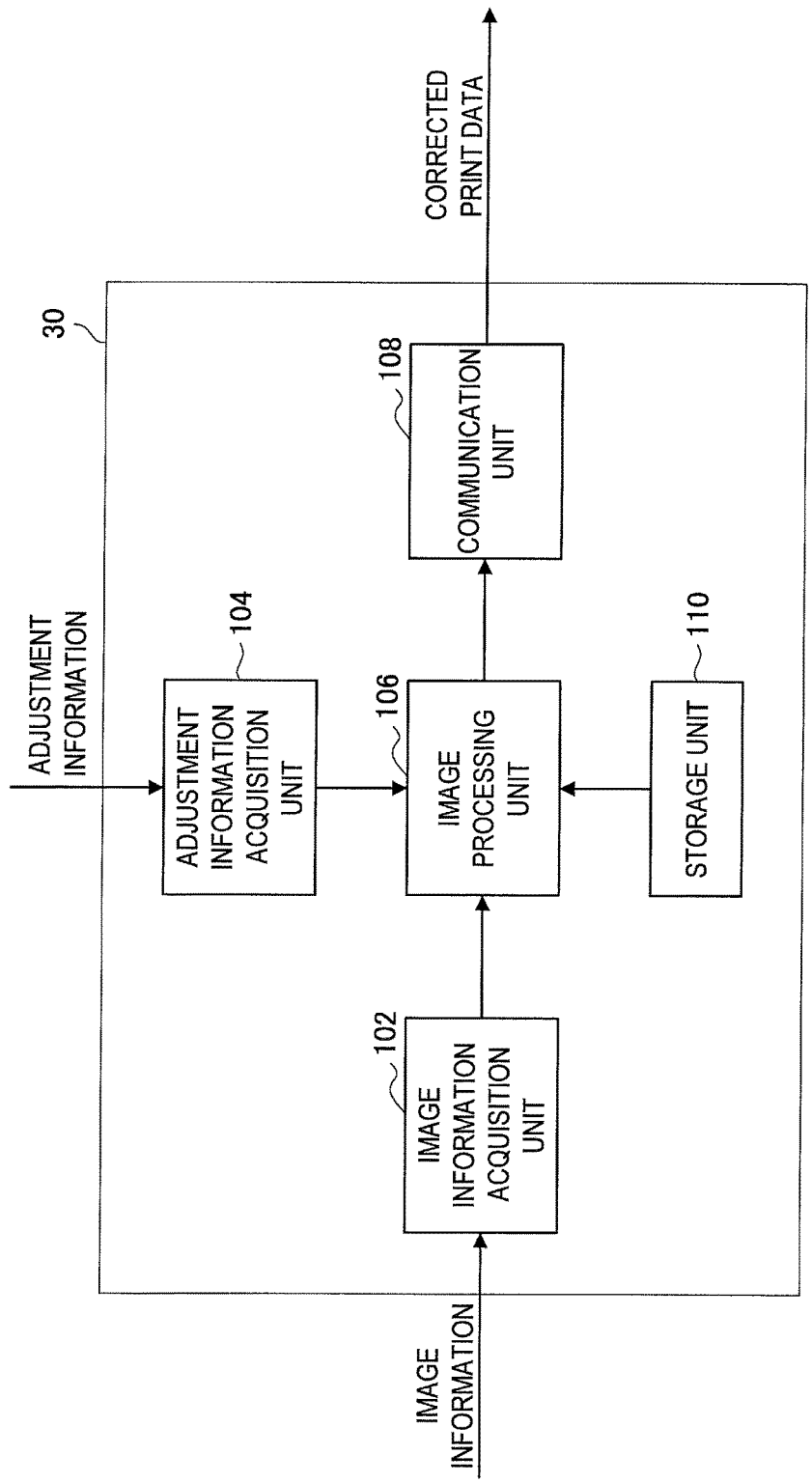
FIG. 2 is a block diagram showing an example of a functional configuration of an image processing device 30 according to the first embodiment.

With reference to FIG. 2, there will be described an example of a functional configuration of the image processing device 30 according to the first embodiment.

FIG. 2 is a block diagram showing the example of the functional configuration of the image processing device 30 according to the first embodiment. As shown in FIG. 2, the image processing device 30 includes an image information acquisition unit 102, an adjustment information acquisition unit 104, an image processing unit 106, a communication unit 108, and a storage unit 110.

(Image Information Acquisition Unit 102)

The image information acquisition unit 102 acquires the captured image from the endoscope 10. The acquired captured image is the same as the image outputted from the endoscope 10 to the monitor 20. The image information acquisition unit 102 outputs the acquired captured image to the image processing unit 106.

(Adjustment Information Acquisition Unit 104)

The adjustment information acquisition unit 104 acquires, from the monitor 20, the adjustment information (for example, color calibration information about color calibration) about the adjustment of the image quality performed in the monitor 20 on which the captured image is displayed. When an instruction to cause the printer 40 to perform printing is issued, the adjustment information acquisition unit 104 acquires the adjustment information from the monitor 20. In addition to the adjustment information, the adjustment information acquisition unit 104 also acquires the device information of the monitor 20. The adjustment information acquisition unit 104 outputs the acquired adjustment information and device information to the image processing unit 106. Although, in the above description, the acquisition of the adjustment information is performed when the instruction to cause the printer 40 to perform printing is issued, the configuration is not limited thereto. For example, adjustment information may be acquired from the monitor 20 every time color calibration is performed in the monitor 20.

(Image Processing Unit 106)

The image processing unit 106 performs image processing on the captured image received from the image information acquisition unit 102. The image processing unit 106 generates, from the captured image, print data that the printer 40 can print. For example, the image processing unit 106 converts the captured image to the print data on the basis of the conversion table for printer (the conversion table 35 shown in FIG. 1). A plurality of conversion tables may be stored in the storage unit 110. In this case, the image processing unit 106 chooses a conversion table corresponding to the printer 40 on the basis of the device information acquired by the adjustment information acquisition unit 104.

On the basis of the adjustment information acquired by the adjustment information acquisition unit 104, the image processing unit 106 performs, on the print data, correction that is corresponding to the adjustment in the monitor 20. The image processing unit 106 functions as a correction value acquisition unit to acquire a correction value used for performing, on the print data, correction that is corresponding to image quality adjustment (for example, color calibration) based on the acquired adjustment information. Accordingly, the correction value that is corresponding to the image quality adjustment of the monitor 20 can be automatically acquired.

In the first embodiment, the image processing unit 106 functions as a correction unit to perform, on the print data, correction that is based on the acquired correction value and is corresponding to adjustment (for example, color calibration) in the monitor 20. Accordingly, the print data that is corrected on the basis of the adjustment in the monitor 20 can be generated.

Figure 3:
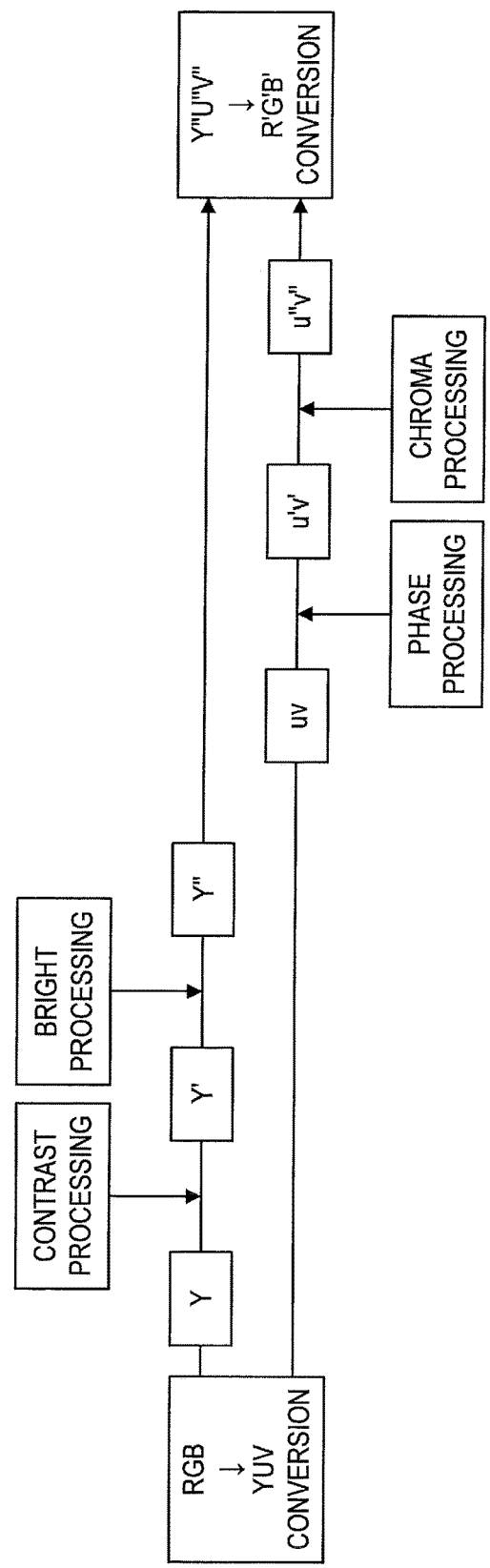
FIG. 3 is a diagram illustrating an overview of a flow of print-data correction processing according to the first embodiment.

With reference to FIG. 3, there will be described a flow of correction processing performed on the print data by the image processing unit 106.

FIG. 3 is a diagram illustrating an overview of a flow of print-data correction processing according to the first embodiment. Here, it is assumed that the captured image input from the image information acquisition unit 102 to the image processing unit 106 is a so-called RGB format image. First, the image processing unit 106 converts the captured image in RGB format to an image in YUV format. Here, data Y represents a luminance component and data U and data V represent chrominance components.

Subsequently, the image processing unit 106 performs, on the data Y, contrast processing and/or bright processing that are shown in FIG. 4, and acquires data Y". FIG. 4 is a schematic view illustrating the constant processing and the bright processing. Here, "Contrast" represents differences in brightness, and "Bright" represents brightness. In graphs of FIG. 4, a horizontal axis represents input and a vertical axis represents output. Note that, the fact that the horizontal axis represents values within a range of 0 to 255 (8-bit) and the vertical axis represents values over 255 attributes to emissions of light by the backlight of the monitor 20. As seen from FIG. 4, an output value with respect to an input becomes larger when values of Contrast or Bright become larger.

The image processing unit 106 performs, on the data U and the data V, phase processing and chroma processing that are shown in FIG. 5 so as to acquire data U" and data V". FIG. 5 is a schematic view illustrating the phase processing and the chroma processing. Here, "Phase" represents phases, and "Chroma" represents chroma. As seen from FIG. 5, a phase is changed in accordance with a numerical value of "Phase", and a diameter is changed in accordance with a numerical value of "Chroma". By performing the above-described four processes, the same correction as the adjustment in the monitor 20 is performed.

Subsequently, in order to transmit data to the printer 40, the image processing unit 106 changes the data in YUV format into data R', data G', and data B' that are in RGB format. Accordingly, the captured image is changed (corrected) into print data having the same image quality as an image quality adjusted in the monitor 20.

(Communication Unit 108)

The communication unit 108 transmits/receives data to/from the printer 40. For example, the communication unit 108 is a transmission unit to transmit, to the printer 40, the print data corresponding to the captured image. In the first embodiment, the communication unit 108 transmits, to the printer 40, the print data corrected by the image processing unit 106 on the basis of the correction value when the user adjusts the image quality in the monitor 20. Accordingly, the printer 40 prints an image having the same image quality as the image quality adjusted in the monitor 20.

(Storage Unit 110)

The storage unit 110 stores a program relating to processing performed by the image processing device 30 (for example, program relating to below-described correction processing of print data) and various types of data. The storage unit 110 stores the above-described conversion table for a printer. In addition, the storage unit 110 may store the above-described captured image, adjustment information, and device information.

(1-3. Operation Example of Image Processing Device)

Figure 6:
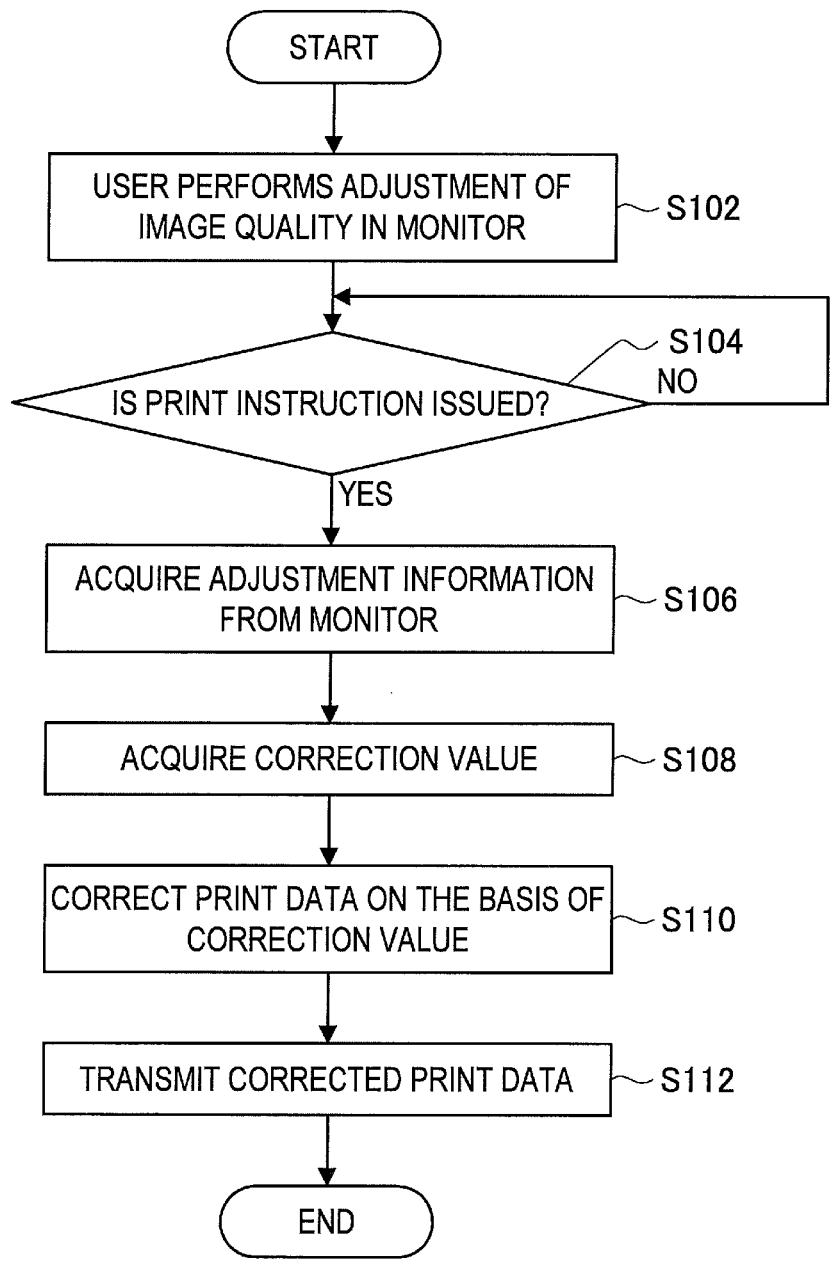
FIG. 6 is a flowchart showing an operation example of the image processing device 30 according to the first embodiment.

With reference to FIG. 6, there will be described an operation example of the image processing device 30 according to the first embodiment. FIG. 6 is a flowchart showing an operation example of the image processing device 30 according to the first embodiment.

The flowchart in FIG. 6 starts at a time after the user performs adjustment (here, color calibration) of the image quality in the monitor 20 (step S102). Note that, when the monitor 20 displays the image captured by the endoscope 10, the image information acquisition unit 102 of the image processing device 30 acquires the identical image from the endoscope 10.

Subsequently, the user issues a print instruction to print the image displayed on the monitor 20 (YES in step S104), and then the adjustment information acquisition unit 104 acquires the adjustment information from the monitor 20 (step S106).

Subsequently, on the basis of the adjustment information, the image processing unit 106 acquires the correction value used for correcting the print data to be the same quality as the image quality adjusted in the monitor 20 (step S108). Then, the image processing unit 106 corrects the print data on the basis of the correction value (step S110).

Subsequently, the communication unit 108 transmits the corrected print data to the printer 40 (step S112). The printer 40 performs print based on the received print data. In this way, even if the user does not change the settings of the printer 40, the image quality of the printed image becomes the same as the image quality adjusted in the monitor 20.

2. Second Embodiment

Figure 7:
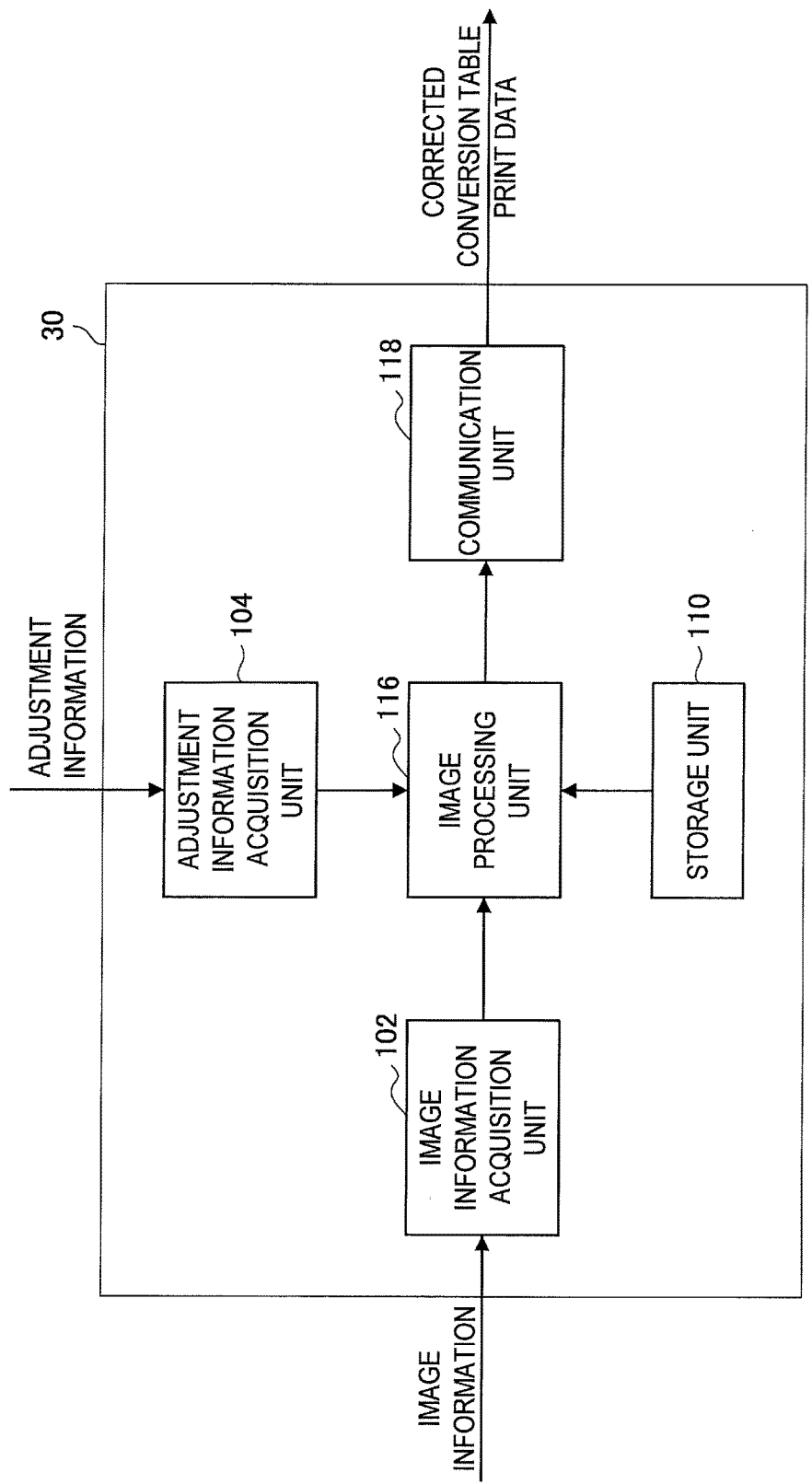
FIG. 7 is a block diagram showing an example of a functional configuration of an image processing device 30 according to a second embodiment.

With reference to FIG. 7, a second embodiment will be described. Hereinafter, there will be mainly described a configuration different from the first embodiment, and the description similar to the configuration of the first embodiment will be omitted.

FIG. 7 is a block diagram showing an example of a functional configuration of an image processing device 30 according to the second embodiment. Processing in an image processing unit 116 and a communication unit 118 according to the second embodiment differ from that of the first embodiment.

In the first embodiment, the image processing unit 106 corrects, on the basis of the correction value, the print data to be the image quality corresponding to the adjustment in the monitor 20. However, in the second embodiment, the image processing unit 116 does not correct print data. Instead, the image processing unit 116 functions as a correction unit to correct, on the basis of a correction value, the conversion table (conversion table 35 shown in FIG. 1) used for converting a captured image to print data.

In the first embodiment, the communication unit 108 transmits the corrected print data to the printer 40 when the user adjusts the image quality in the monitor 20. On the other hand, in the second embodiment, a communication unit 118 transmits the corrected conversion table and the print data to the printer 40 when the user adjusts the image quality in the monitor 20. In this case, the printer 40 corrects the print data on the basis of the corrected conversion table, and then performs printing. As a result, in the second embodiment, the printer 40 also prints an image having the same image quality as the image quality adjusted in the monitor 20.

Figure 8:
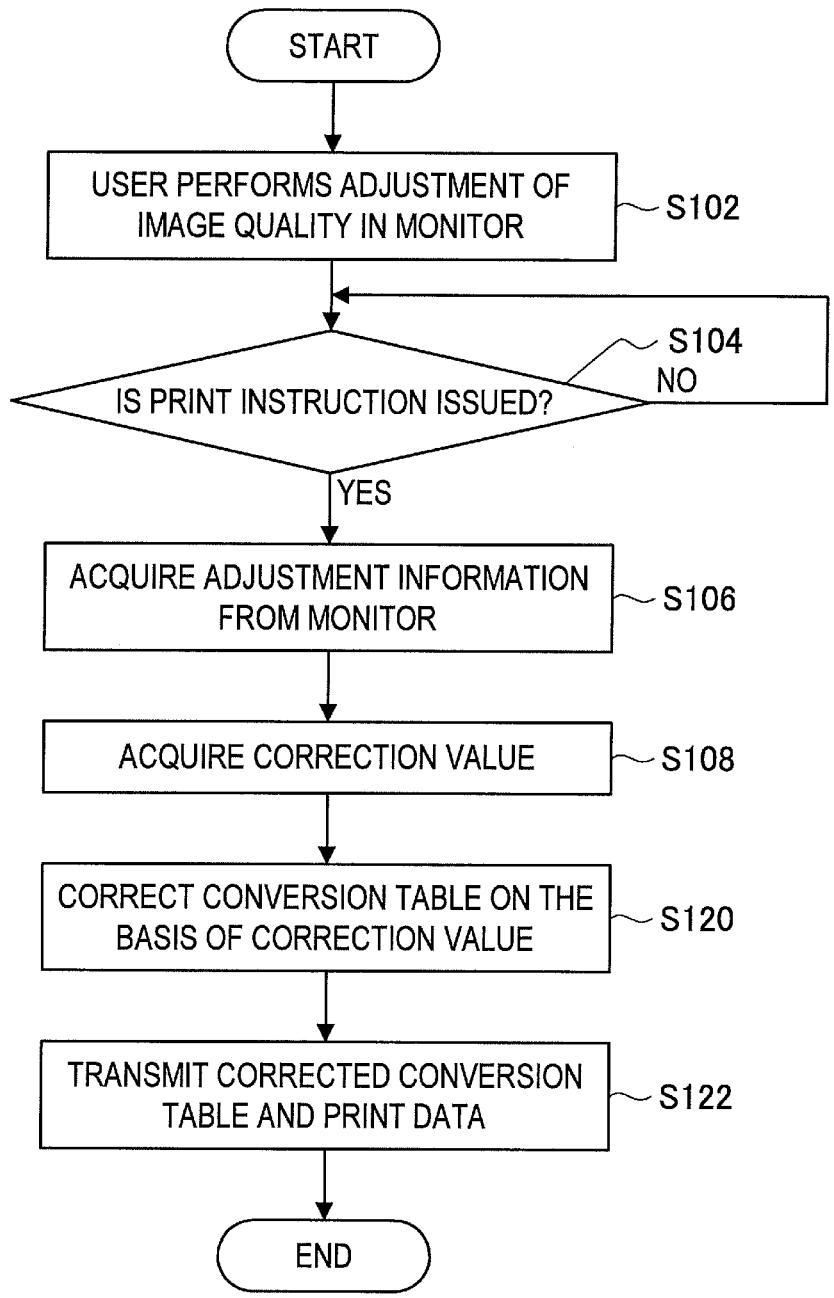
FIG. 8 is a flowchart showing an operation example of the image processing device 30 according to the second embodiment.

Hereinafter, with reference to FIG. 8, there will be described an operation example of the image processing device 30 according to the second embodiment. FIG. 8 is a flowchart showing the operation example of the image processing device 30 according to the second embodiment.

The descriptions of steps S102 to S108 shown in FIG. 8 are omitted because the descriptions are the same as those of FIG. 6. The image processing unit 116 corrects the conversion table on the basis of the acquired correction value (step S120).

Subsequently, the communication unit 118 transmits the corrected conversion table and the print data to the printer 40 (step S122). The printer 40 corrects the print data on the basis of the received conversion table, and then performs printing based on the corrected print data. In this way, even if the user does not change the settings of the printer 40, the image quality of the printed image becomes the same as the image quality adjusted in the monitor 20.

Although, in the above description, the image processing device 30 corrects the conversion table on the basis of the correction value, the configuration is not limited thereto. For example, it may be possible that the printer 40 previously includes the conversion table and the image processing device 30 transmits the correction value and the print data to the printer 40. In this case, it may be possible that the printer 40 corrects the conversion table on the basis of the received correction value, and then corrects the print data. It may also be possible that the printer 40 corrects the print data on the basis of the received correction value and the previously-included conversion table.

3. Third Embodiment

Figure 9:
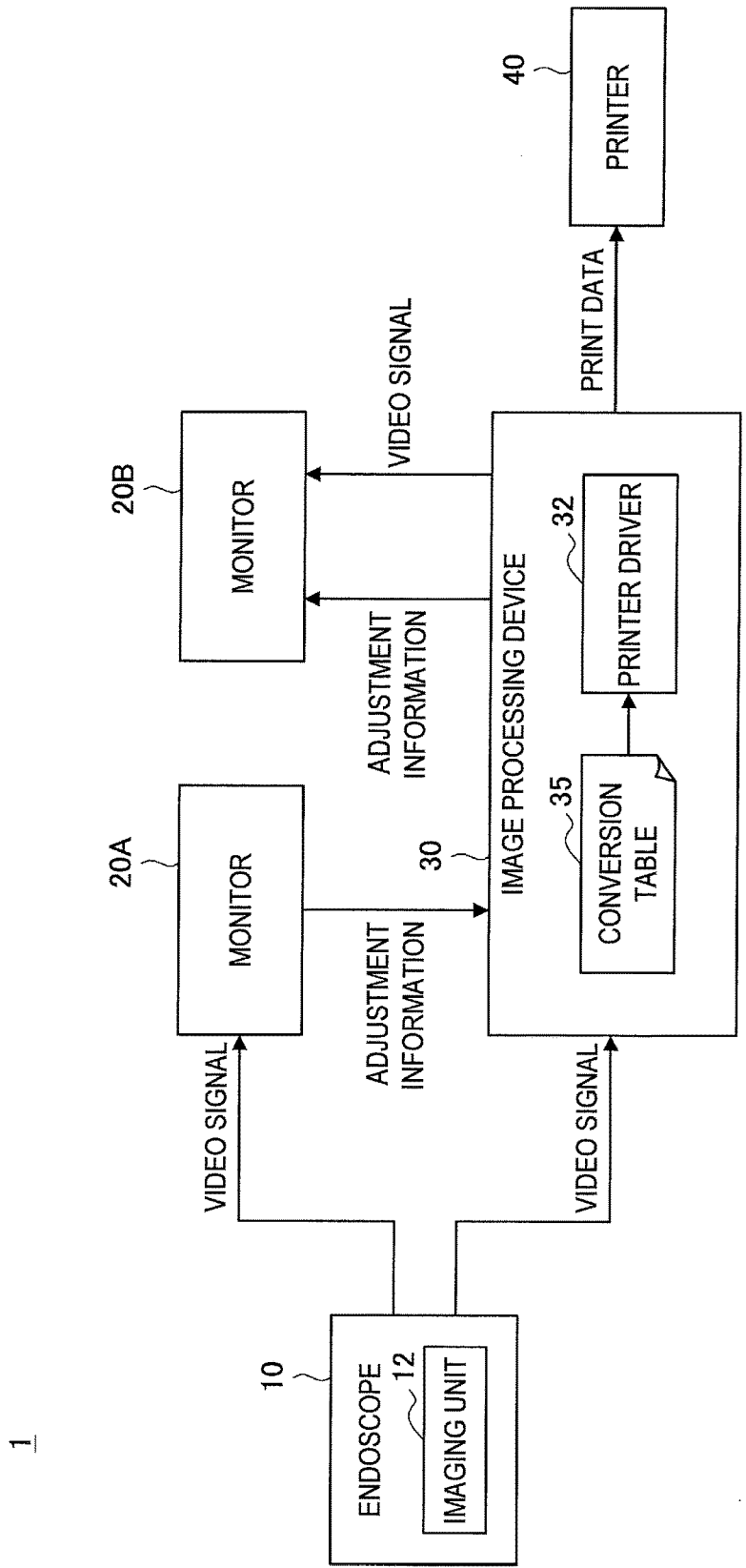
FIG. 9 is a block diagram showing an example of a schematic configuration of an endoscope system 1 according to a third embodiment.

With reference to FIG. 9, a third embodiment will be described. Hereinafter, there will be mainly described a configuration different from the first embodiment, and the description similar to the configuration of the first embodiment will be omitted.

FIG. 9 is a block diagram showing an example of a schematic configuration of an endoscope system 1 according to the third embodiment. In the above described first embodiment, the endoscope system 1 includes a single monitor 20. However, in the third embodiment, the endoscope system 1 includes two monitors 20A and 20B. Note that, the monitor 20A and the monitor 20B correspond to a first display device and a second display device, respectively.

In the third embodiment, an image captured by the endoscope 10 can be displayed on the monitor 20A and the monitor 20B. Here, the monitor 20A directly receives the captured image (video signal) from the endoscope 10 and displays the captured image, and the monitor 20B receives the captured image (video signal) through the image processing device 30 and displays the captured image. It may be possible that the monitor 20B also directly receives the captured image from the endoscope 10.

When there are two monitors 20A and 20B, the user may perform adjustment (color calibration) of an image quality of one (here, the monitor 20A) of the monitors. When the image quality is adjusted in the single monitor 20A, the image processing device 30 according to the third embodiment adjusts an image quality in the monitor 20B to be the same as the image quality in the monitor 20A.

The details will be described below. When the user adjusts the image quality in the monitor 20A, the adjustment information acquisition unit 104 of the image processing device 30 (see FIG. 2) acquires adjustment information about adjustment of the image quality from the monitor 20A. Subsequently, the communication unit 108 (see FIG. 2) transmits the acquired adjustment information to the monitor 20B. The monitor 20B adjusts the image quality on the basis of the received adjustment information. In this way, when an image quality in one of two monitors is adjusted, an image quality in the other monitor is automatically adjusted in the same way. Accordingly, the user does not have to manually adjust the image qualities in the two monitors.

4. Hardware Configuration

The above-described operations of the image processing device 30 may be achieved by cooperation of a hardware configuration and software that are included in the image processing device. Hereinafter, the hardware configuration of the image processing device will be described.

Figure 10:
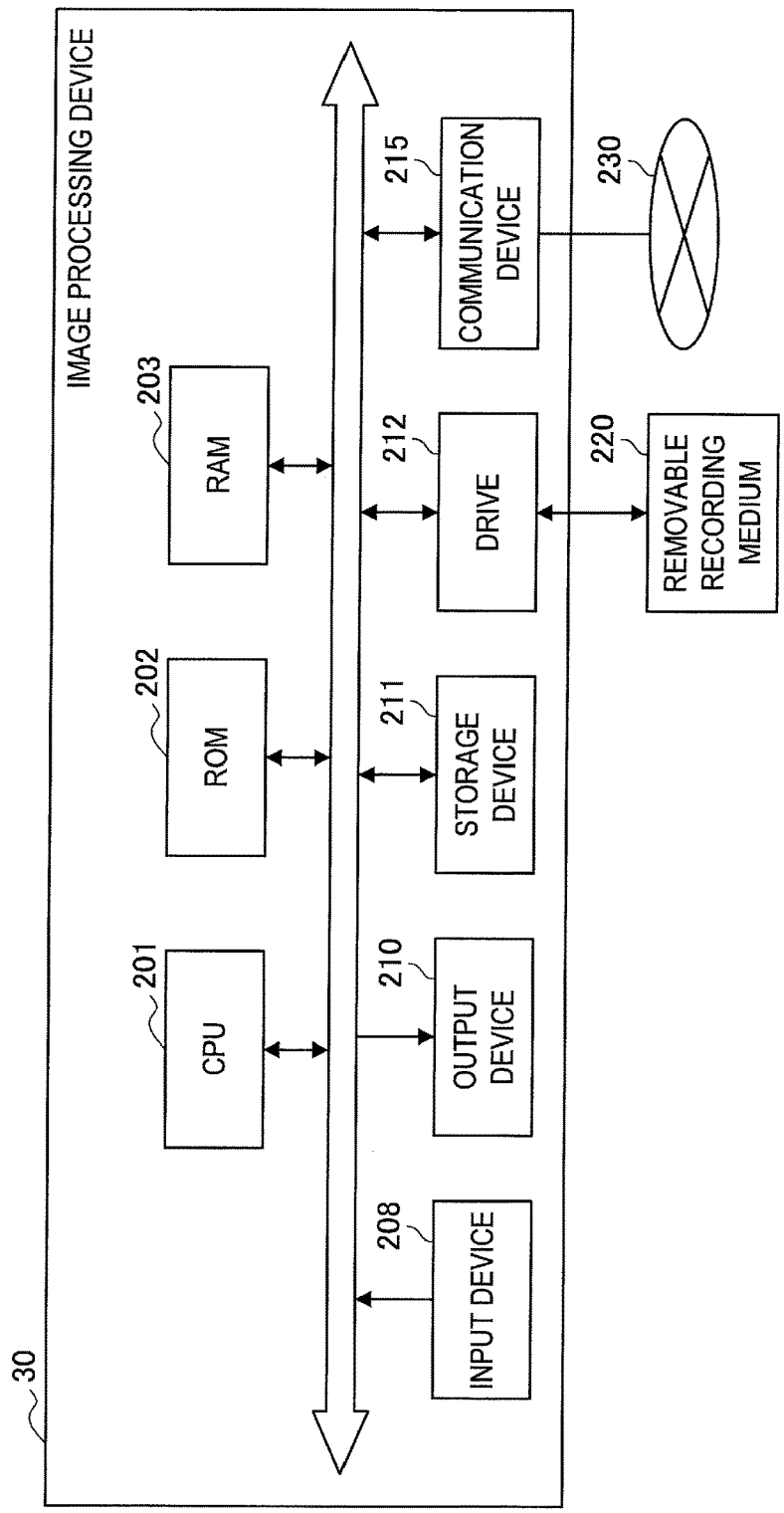
FIG. 10 is a block diagram showing a hardware configuration example of an image processing device 30.

FIG. 10 is a block diagram showing a hardware configuration example of the image processing device 30. As shown in FIG. 10, the image processing device 30 includes a central processing unit (CPU) 201, read only memory (ROM) 202, random access memory (RAM) 203, an input device 208, an output device 210, a storage device 211, a drive 212, and a communication device 215.

The CPU 201 serves as an operation processor and a controller, and controls all operations in the image processing apparatus 30 in accordance with various programs. The CPU 201 may be a microprocessor. The ROM 202 stores programs and operation parameters which are used by the CPU 201. The RAM 203 temporarily stores program which are used in the execution of the CPU 201, parameters which is appropriately modified in the execution, and the like. They are connected with each other via a host bus configured from a CPU bus or the like.

The input device 208 is constituted of an input means for the user to input information, such as a mouse, a keyboard, a touch panel, a button, a microphone, a switch, and a lever, an input control circuit that generates an input signal on the basis of an input by the user and outputs the input signal to the CPU 201, and the like. By operating the input device 208, the user of the image processing device 30 can input various types of data into the image processing device 30 and instruct the image processing device 30 to execute processing operations.

The output device 210 includes a display device such as a liquid crystal display (LCD) device, an organic light emitting diode (OLED) device, and a lamp. The output device 210 further includes an audio output device such as a speaker and headphones. For example, the display device displays a captured image, a generated image, and the like. The audio output device converts audio data or the like to audio and outputs the audio.

The storage device 211 is a data storage device as an example of the storage unit of the image processing device 30 according to the embodiments of the present disclosure. The storage device 211 may include a recording medium, a recording device for recording data in the recording medium, a reading device for reading the data from the recording medium, a deleting device for deleting the data recorded in the recording medium, and the like. This storage device 211 stores programs executed by the CPU 201 and various data.

The drive 212 is a reader/writer for a recording medium, which is embedded in the image processing device 30 or provided as an external device. The drive 212 reads information recorded in a removable recording medium 220 that is mounted, such as a magnetic disk, an optical disc, a magneto optical disk, and semiconductor memory, and outputs the information to the RAM 203. The drive 212 can also write information on the removable recording medium 220.

The communication device 215 is, for example, a communication interface including a communication device and the like for connecting with a network 230. The communication device 215 may be a wired communication device for performing wired communication, or may be a wireless local area network (LAN) capable communication device.

5. Conclusion

As described above, the image processing device 30 acquires color calibration information about color calibration performed in the monitor 20, and acquires a correction value used for performing, on print data to be printed by the printer 40, correction that is corresponding to the color calibration in the monitor 20. Accordingly, the image processing device 30 or the printer 40 corrects the print data on the basis of the correction value, and the printer 40 prints the corrected print data.

In the above-described configurations, a result of adjustment in the monitor 20 is automatically reflected in a print result of the printer 40. Accordingly, the user does not have to compare the monitor 20 with the print result and perform color calibration in the printer 40 by trial and error. In addition, sheets of paper used for the color calibration of the printer 40 can be prevented from being wasted. Moreover, a help from a support person becomes not necessary.

It should be understood by those skilled in the art that various modifications, combinations, sub-combinations and alterations may occur depending on design requirements and other factors insofar as they are within the scope of the appended claims or the equivalents thereof.

The steps shown in the flowcharts in the above-described embodiments includes not only processing chronologically performed on the basis of the described order, but also processing that are not necessarily performed in a chronological order and may be executed in a parallel manner or in an individual manner. Needless to say, the order of steps to be chronologically processed can be appropriately changed depending on the situation.

The processing in the image processing device described in the embodiments of the present disclosure may be achieved by any of software, hardware, or a combination of software and hardware. The programs configuring the software are previously stored in a storage medium provided inside or outside each device, for example. Each program is read in random access memory (RAM) during execution and is executed by a processor such as a central processing unit (CPU).

Additionally, the present technology may also be configured as below.

(1) An image processing device including:
an image information acquisition unit configured to acquire a captured image from an endoscope;
an adjustment information acquisition unit configured to acquire color calibration information about color calibration performed in a display device on which the captured image is displayed;
a transmission unit configured to transmit, to a printing device, print data corresponding to the acquired captured image; and
a correction value acquisition unit configured to acquire a correction value used for performing, on the print data, correction that is corresponding to the color calibration of the acquired color calibration information.

(2) The image processing device according to (1), further including:
a correction unit configured to perform, on the print data, correction corresponding to the color calibration on a basis of the correction value.

(3) The image processing device according to (2),
wherein the transmission unit transmits, to the printing device, print data corrected by the correction unit on a basis of the correction value.

(4) The image processing device according to (1), further including:
a correction unit configured to correct, on a basis of the correction value, a conversion table used for converting the captured image to the print data.

(5) The image processing device according to (4),
wherein the transmission unit transmits the corrected conversion table and the corrected print data to the printing device.

(6) The image processing device according to any one of (1) to (5),
wherein, when an instruction to cause the printing device to perform printing is issued, the adjustment information acquisition unit acquires the color calibration information.

(7) The image processing device according to any one of (1) to (6),
wherein the captured image is displayed by a first display device and a second display device,
wherein the adjustment information acquisition unit acquires color calibration information about color calibration performed in the first display device, and
wherein the image processing device further includes a second transmission unit configured to transmit the acquired color calibration information to the second display device.

(8) An image processing method including:
acquiring a captured image from an endoscope;
acquiring color calibration information about color calibration performed in a display device on which the captured image is displayed;
transmitting, to a printing device, print data corresponding to the acquired captured image; and
acquiring a correction value used for performing, on the print data, correction that is corresponding to the color calibration of the acquired color calibration information.

(9) A program for causing a computer to execute:
acquiring a captured image from an endoscope;
acquiring color calibration information about color calibration performed in a display device on which the captured image is displayed;
transmitting, to a printing device, print data corresponding to the acquired captured image; and
acquiring a correction value used for performing, on the print data, correction that is corresponding to the color calibration of the acquired color calibration information.

(10) An endoscope system including:
a display device configured to display a captured image captured by an endoscope;
a printing device configured to perform printing; and
an image processing device configured to transmit, to the printing device, print data corresponding to the captured image,
wherein the image processing device includes
an image information acquisition unit configured to acquire the captured image from the endoscope,
an adjustment information acquisition unit configured to acquire color calibration information about color calibration performed in a display device on which the captured image is displayed, and
a correction value acquisition unit configured to acquire a correction value used for performing, on the print data, correction that is corresponding to the color calibration of the acquired color calibration information.

What is claimed is:

1. An image processing device, comprising:
a memory configured to store a plurality of conversion tables; and
one or more processors configured to:
acquire a captured image from an endoscope, wherein the captured image is in a first format;
convert the captured image from the first format into a second format;
obtain first color calibration information about color calibration of the captured image displayed on a first display device, wherein the color calibration is based on a first manual adjustment on the first display device;
transmit the first color calibration information from the first display device to a second display device;
cause the second display device to adjust the color calibration of the second display device to match the color calibration of the first display device based on the first color calibration information from the first display device;
transmit, to a printing device, first print data corresponding to the converted image;
acquire a correction value for correction of the first print data; and
correct, based on the correction value, a conversion table for conversion of the captured image to the first print data,
wherein the conversion table is selected, from the plurality of conversion tables stored in the memory, based on device information.

2. The image processing device according to claim 1, wherein the converted image includes an input value, and wherein the one or more processors are further configured to:
process the input value of the converted image to acquire an output value; and
correct the first print data corresponding to the color calibration based on the correction value.

3. The image processing device according to claim 2, wherein the one or more processors are further configured to transmit, to the printing device, second print data corrected based on the correction value.

4. The image processing device according to claim 3, wherein the one or more processors are further configured to transmit the corrected conversion table and the corrected second print data to the printing device.

5. The image processing device according to claim 2, wherein, based on an issuance of an instruction to cause the printing device to print, the one or more processors are further configured to acquire the first color calibration information.

6. The image processing device according to claim 2, further comprising:
the first display device; and
a backlight of the first display device,
wherein the one or more processors are further configured to control the backlight to emit light based on the input value and the output value.

7. The image processing device according to claim 1, wherein the one or more processors are further configured to:
convert the captured image from the second format into the first format, and
transmit the converted image in the first format to the printing device.

8. The image processing device according to claim 1, wherein the first format comprises a RGB format and the second format comprises a YUV format.

9. The image processing device according to claim 1, wherein the one or more processors are further configured to process a luminance component of the converted image, and
wherein the luminance component comprises one of a brightness component or a contrast component of the converted image.

10. The image processing device according to claim 1, wherein the one or more processors are further configured to process a chrominance component of the converted image, and
wherein the chrominance component comprises one of a phase component or a chroma component of the converted image.

11. The image processing device according to claim 1, wherein the image from the endoscope comprises a video.

12. The image processing device according to claim 1, wherein the one or more processors are further configured to:
obtain second color calibration information about the color calibration of the captured image displayed on the second display device, wherein the color calibration is based on a second manual adjustment on the second display device; and
transmit the second color calibration information from the second display device to the first display device.

13. An image processing method, comprising:
in an image processing device:
acquiring a captured image from an endoscope, wherein the captured image is in a first format;
converting the captured image from the first format into a second format;
obtaining color calibration information about color calibration of the captured image displayed on a first display device, wherein the color calibration is based on a manual adjustment on the first display device;

transmitting the obtained color calibration information from the first display device to a second display device;

causing the second display device to adjust the color calibration of the second display device to match the color calibration of the first display device based on the color calibration information from the first display device;

transmitting to a printing device, first print data corresponding to the converted image;

acquiring a correction value for correction of the first print data; and correcting, based on the correction value, a conversion table for conversion of the captured image to the first print data,
wherein the conversion table is selected, from a plurality of conversion tables stored in a memory, based on device information.

14. A non-transitory computer-readable medium having stored thereon, computer-executable instructions, which when executed by a computer, cause the computer to execute operations, the operations comprising:

acquiring a captured image from an endoscope, wherein the captured image is in a first format;

converting the captured image from the first format into a second format;

obtaining color calibration information about color calibration of the captured image displayed on a first display device, wherein the color calibration is based on a manual adjustment on the first display device;

transmitting the obtained color calibration information from the first display device to a second display device;

causing the second display device to adjust the color calibration of the second display device to match the color calibration of the first display device based on the color calibration information from the first display device;

transmitting to a printing device, first print data corresponding to the converted image;

acquiring a correction value for correction of the first print data; and correcting, based on the correction value, a conversion table for conversion of the captured image to the first print data,
wherein the conversion table is selected, from a plurality of conversion tables stored in a memory, based on device information.

15. An endoscope system, comprising:

a first display device configured to display a captured image captured by an endoscope;
wherein the captured image is in a first format;

a printing device configured to print the captured image;

a memory configured to store a plurality of conversion tables; and one or more processors configured to:
transmit, to the printing device, print data corresponding to the captured image;
convert the captured image from the first format into a second format;
obtain color calibration information about color calibration of the captured image displayed on the first display device, wherein the color calibration is based on a manual adjustment on the first display device;
transmit the obtained color calibration information from the first display device to a second display device;
cause the second display device to adjust the color calibration of the second display device to match the color calibration of the first display device based on the color calibration information from the first display device;
transmit, to the printing device, first print data corresponding to the converted image;
acquire a correction value for correction of the first print data; and
correct, based on the correction value, a conversion table for conversion of the captured image to the first print data,
wherein the conversion table is selected, from the plurality of conversion tables stored in the memory, based on device information.

* * * * *